US012728138B1

(12) United States Patent
Phadke et al.

(10) Patent No.: US 12,728,138 B1
(45) **Date of Patent: *Sep. 8, 2026**

(54) AQUEOUS ORAL COMPOSITIONS INCLUDING POTASSIUM CHLORIDE

(71) Applicant: GENUS LIFESCIENCES INC., Allentown, PA (US)

(72) Inventors: Shivaji Phadke, Berkeley Heights, NJ (US); Vaishnavi Parikh, Sellersville, PA (US)

(73) Assignee: GENUS LIFESCIENCES INC., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/438,952

(22) Filed: Jan. 2, 2026

Related U.S. Application Data

(63) Continuation of application No. 18/504,280, filed on Nov. 8, 2023, now Pat. No. 12,539,314, which is a continuation of application No. 17/660,499, filed on Apr. 25, 2022, now abandoned, which is a continuation of application No. 16/295,215, filed on Mar. 7, 2019, now abandoned.

(51) Int. Cl.

| | |
|---|---|
| ***A61K 33/14*** | (2006.01) |
| ***A61K 9/00*** | (2006.01) |
| ***A61K 9/08*** | (2006.01) |
| ***A61K 47/10*** | (2017.01) |
| ***A61K 47/12*** | (2006.01) |
| ***A61K 47/24*** | (2006.01) |
| ***A61K 47/26*** | (2006.01) |

(52) U.S. Cl.
CPC ............ *A61K 33/14* (2013.01); *A61K 9/0053* (2013.01); *A61K 9/08* (2013.01); *A61K 47/10* (2013.01); *A61K 47/12* (2013.01); *A61K 47/24* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,970,750 | A | 7/1976 | Brockemeyer et al. |
| 4,259,315 | A | 3/1981 | Lippmann et al. |
| 4,259,323 | A | 3/1981 | Ranucci |
| 4,352,791 | A | 10/1982 | Zaffaroni et al. |
| 4,582,705 | A | 4/1986 | Primes et al. |
| 4,723,957 | A | 2/1988 | Magruder et al. |
| 4,747,847 | A | 5/1988 | Magruder et al. |
| 5,035,898 | A | 7/1991 | Chang et al. |
| 5,066,483 | A | 11/1991 | Harkrader et al. |
| 5,284,648 | A | 2/1994 | White et al. |
| 5,449,522 | A | 9/1995 | Hill |
| 5,505,962 | A | 4/1996 | Sparks |
| 5,780,055 | A | 7/1998 | Habib et al. |
| 6,199,698 | B1 | 3/2001 | Hetrick |
| 6,365,182 | B1 | 4/2002 | Khankari et al. |
| 6,780,437 | B2 | 8/2004 | Christenson et al. |
| 6,793,935 | B2 | 9/2004 | Hermelin et al. |
| 6,899,899 | B2 | 5/2005 | Takagi et al. |
| 7,056,534 | B2 | 6/2006 | Christenson et al. |
| 7,189,415 | B2 | 3/2007 | Takagi et al. |
| 7,566,463 | B2 | 7/2009 | Ayala |
| 8,685,483 | B2 | 4/2014 | Knight |
| 8,691,190 | B2 | 4/2014 | Haught et al. |
| 8,771,749 | B2 | 7/2014 | Oda et al. |
| 9,763,464 | B2 | 9/2017 | Hoejvang-Nielsen |
| 9,795,636 | B2 | 10/2017 | Oda et al. |
| 11,071,739 | B1 | 7/2021 | Parikh |
| 12,539,314 | B1 | 2/2026 | Phadke et al. |
| 2002/0031547 | A1 | 3/2002 | Takagi et al. |
| 2003/0072719 | A1 | 4/2003 | Nelson et al. |
| 2003/0104070 | A1 | 6/2003 | Christenson et al. |
| 2003/0108605 | A1 | 6/2003 | Hermelin et al. |
| 2005/0170020 | A1 | 8/2005 | Medasani et al. |
| 2007/0014856 | A1 | 1/2007 | Takagi et al. |
| 2009/0017167 | A1 | 1/2009 | Krumhar et al. |
| 2010/0303853 | A1 | 12/2010 | Lejeune et al. |
| 2011/0300266 | A1 | 12/2011 | Rinaldi et al. |
| 2012/0003163 | A1 | 1/2012 | Mordas |
| 2015/0290112 | A1 | 10/2015 | Nesta et al. |
| 2017/0056441 | A1 | 3/2017 | Adeniji et al. |

(Continued)

FOREIGN PATENT DOCUMENTS

| | | | |
|---|---|---|---|
| CN | 103479664 | A | 1/2014 |
| WO | 2017/150715 | A1 | 9/2017 |

(Continued)

OTHER PUBLICATIONS

USPTO artificial intelligence top results, printed 2026 (Year: 2026).*
Potassium Chloride—potassium chloride solution (Pharmaceutical Associates, Inc.) (Revised: Jan. 2015).
Potassium Chloride—potassium chloride solution (Amneal Pharmaceuticals LLC) (Revised: Jun. 2017).
Potassium Chloride—potassium chloride solution (Apotex Corp) (Revised: Feb. 2018).
Potassium Chloride oral solution (Genus Lifesciences Inc.) (Revised: Feb. 2019).
Potassium Chloride—potassium chloride solution (Lupin Pharmaceuticals, Inc.) (Revised: Oct. 2018).
Potassium Chloride—potassium chloride solution (Novel Laboratories, Inc.) (Revised: Nov. 2018).
Potassium Chloride—potassium chloride solution (Par Pharmaceutical) (Revised: Apr. 2018).
Potassium Chloride—potassium chloride solution (VistaPharm, Inc.) (Revised: Jun. 2017).
Potassium Chloride Oral Solution, USP 20%, https://dailymed.nlm.nih.gov/dailymed/fda/fdaDrugXsl.cfm?setid=6d2cec16-3127-49b5-9cb1-840 . . . , accessed Jan. 11, 2019, 6 pages.

(Continued)

*Primary Examiner* — Bennett M Celsa
*Assistant Examiner* — Alissa Prosser
(74) *Attorney, Agent, or Firm* — K&L Gates LLP

(57) ABSTRACT

Disclosed are oral liquid compositions comprising potassium chloride, glycerin, sodium benzoate, buffer, and water. The compositions are aqueous, free of alcohol and parabens, and exhibit enhanced stability with no visible formation of precipitates after temperature cycling and light exposure. The compositions are useful for the treatment of hypokalemia in patients with or without metabolic alkalosis.

6 Claims, No Drawings

(56) References Cited

U.S. PATENT DOCUMENTS

2017/0333561 A1 11/2017 Alley
2019/0069578 A1 3/2019 Washio

FOREIGN PATENT DOCUMENTS

WO 2018/043275 A1 3/2018
WO 2023230636 A2 11/2023

OTHER PUBLICATIONS

Prescribing Information, K-10, Potassium Chloride Oral Solution, 10% USP, Potassium Replacement Therapy, GlaxoSmithKline Inc., Ontario, Canada, Aug. 30, 2017, 10 pages.
Potassium Chloride Oral Solution, USP, https://dailymed.nlm.nih.gov/dailymed/fda/fdaDrugXsl.cfm?setid=aacd46d1-8e11-4a82-80bb-a9c . . . , accessed Jan. 11, 2019, 3 pages.
Ogochukwu et al. "Effect of some preservatives on the aqueous stability of an oral rehydration salt solution intended for use in developing countries, Asian Journal of Pharmaceutical and Clinical Research", 6(2):33-37, 2013.
Allen et al., "Proabsorptive effect of glycerol as a glucose substitute in oral rehydration solutions", Journal of Nutritional Biochemistry, 10:49-55, 1999.
Barreuther et al., "Palatability comparison of oral potassium chloride solutions", American Journal of Hospital Pharmacy 34:1090-1092, 1977.
USPTO artificial intelligence top results, printed 2025.
Joshi et al., "Concentration, temperature, and pH dependence of sunset-yellow aggregates in aqueous solutions: An x-ray investigation", Physical Review E 80, 041703-1-041703-8, 2009.
U.S. Appl. No. 16/295,215, filed Mar. 7, 2019.
U.S. Appl. No. 17/660,499, filed Apr. 25, 2022.
U.S. Appl. No. 18/791,715, filed Aug. 1, 2024.
U.S. Appl. No. 19/411,523, filed Dec. 8, 2025.
Blanco et al., Effect of colloidal silicon dioxide and moisture on powder flow properties: Predicting in-process performance using image-based analysis, International Journal of Pharmaceuticals, 597, Feb. 2, 2021, 7 pages.
FDA Prescribing Information, Potassium Chloride, Revision Jul. 2019, accessed Mar. 7, 2026, at https://www.accessdata.fda.gov/drugsatfda_docs/label/2024/206814lbl.pdf; 2019, 6 pages.
Vachon Lachance et al., Potassium chloride caking tendency: A parmetric study of cake break energy, Advanced Power Technology, 29, 2018, pp. 2140-2152.

* cited by examiner

AQUEOUS ORAL COMPOSITIONS INCLUDING POTASSIUM CHLORIDE

FIELD OF THE DISCLOSURE

Provided herein are aqueous oral compositions including potassium chloride with enhanced stability. Also provided herein are methods of using aqueous oral compositions including potassium chloride for the treatment of hypokalemia in patients with or without metabolic alkalosis.

BACKGROUND

Potassium chloride is known in the art for the treatment and prophylaxis of hypokalemia. While potassium chloride can be administered as oral solid tablets, high concentrations of potassium chloride, as can be imposed with solid oral tablets, may produce gastric upset. To minimize gastric upset, potassium chloride can be administered as an oral solution. Oral potassium chloride solutions, however, have other drawbacks. For example, while solid oral tablets are not particularly vulnerable to bacterial contamination, oral solutions are. Conventionally, bacterial contamination of an oral liquid formulation is prevented by adding a bacteriostatic or bactericidal amount of ethanol. However, the safety of alcohol as an excipient in pharmaceuticals intended for use in children, and particularly those intended for use in very young children, is a significant concern, even when relatively low alcohol concentrations (e.g., less than 0.5%) are present.

As an alternative to alcohol, paraben (e.g., methylparaben, ethylparaben, propylparaben, butylparaben, heptylparaben, etc.) can be used. While parabens adequately control bacterial growth, they can be poorly water soluble, particularly in water below 50° C. or when subjected to storage or temperature cycling conditions. Such compounds may thus produce a cloudy or pharmaceutically-inelegant formulation which can be mistaken as being defective or contaminated.

Accordingly, there remains a need for potassium chloride oral solutions that are free of alcohol and that demonstrate stability upon storage and temperature cycling conditions.

SUMMARY

Provided herein are stable aqueous oral compositions including potassium chloride. The compositions are liquid compositions. In one aspect of the present disclosure, which may be combined with any other aspect or embodiment listed herein unless specified otherwise, the disclosure provides an aqueous oral composition comprising: about 10% to about 20% (w/v) potassium chloride; about 1% to about 5% (w/v) glycerin; about 0.02% to about 0.2% (w/v) sodium benzoate; buffer, and water; wherein the composition is a solution, is free of alcohol, and has no visible formation of precipitates after being subjected to temperature cycling.

In another aspect of the present disclosure, which may be combined with any other aspect or embodiment listed herein unless specified otherwise, the composition comprises: about 10% (w/v) potassium chloride; about 1% to about 3% (w/v) glycerin; about 0.02% to about 0.1% (w/v) sodium benzoate, buffer, and water.

In another aspect of the present disclosure, which may be combined with any other aspect or embodiment listed herein unless specified otherwise, the composition comprises: about 20% (w/v) potassium chloride; about 3% to about 5% (w/v) glycerin; about 0.05% to about 0.2% (w/v) sodium benzoate, buffer, and water.

In another aspect of the present disclosure, which may be combined with any other aspect or embodiment listed herein unless specified otherwise, the composition further comprises a sweetener. In another aspect of the present disclosure, which may be combined with any other aspect or embodiment listed herein unless specified otherwise, the sweetener comprises sucralose.

In another aspect of the present disclosure, which may be combined with any other aspect or embodiment listed herein unless specified otherwise, the buffer comprises a citrate/citric acid buffer.

In another aspect of the present disclosure, which may be combined with any other aspect or embodiment listed herein unless specified otherwise, the composition has no visible formation of precipitates after being subjected to three freeze-thaw cycles, wherein each freeze-thaw cycle comprises: (i) maintaining the composition at a temperature of about −20° C. to about −10° C. for about two days; followed by (ii) maintaining the composition at a temperature of about 40° C. and about 75% relative humidity for about two days.

In another aspect of the present disclosure, which may be combined with any other aspect or embodiment listed herein unless specified otherwise, the composition has no visible formation of precipitates after being subjected to three freeze-thaw cycles, wherein each freeze-thaw cycle comprises: (i) maintaining the composition at a temperature of about −20° C. to about −10° C. for about two days; followed by (ii) maintaining the composition at a temperature of about 25° C. and about 60% relative humidity for about two days.

In another aspect of the present disclosure, which may be combined with any other aspect or embodiment listed herein unless specified otherwise, the composition has no visible formation of precipitates after being subjected to three thermal cycles, wherein each thermal cycle comprises: (i) maintaining the composition at a temperature of about 2° C. to about 8° C. for about two days; followed by (ii) maintaining the composition at a temperature of about 40° C. and about 75% relative humidity for about two days.

In another aspect of the present disclosure, which may be combined with any other aspect or embodiment listed herein unless specified otherwise, the composition has no visible formation of precipitates after being subjected to three thermal cycles, wherein each thermal cycle comprises: (i) maintaining the composition at a temperature of about 2° C. to about 8° C. for about two days; followed by (ii) maintaining the composition at a temperature of about 25° C. and about 60% relative humidity for about two days.

In another aspect of the present disclosure, which may be combined with any other aspect or embodiment listed herein unless specified otherwise, the composition has no visible formation of precipitates after exposure to cool white fluorescent light for about 1.2 million lux hours, followed by exposure to near ultraviolet light for 200 watt hours/square meter.

In another aspect of the present disclosure, which may be combined with any other aspect or embodiment listed herein unless specified otherwise, the composition contains an initial amount of potassium chloride, and after exposure of the composition to cool white fluorescent light for about 1.2 million lux hours, followed by exposure to near ultraviolet light for about 200 watt hours/square meter to obtain a light-treated composition, the light-treated composition contains potassium chloride in an amount that is no more than 3% different from the initial amount of potassium chloride.

In another aspect of the present disclosure, which may be combined with any other aspect or embodiment listed herein unless specified otherwise, the composition contains an initial amount of sodium benzoate, and after exposure of the composition to cool white fluorescent light for about 1.2 million lux hours, followed by exposure to near ultraviolet light for about 200 watt hours/square meter to obtain a light-treated composition, the light-treated composition contains sodium benzoate in an amount that is no more than 5% different from the initial amount of sodium benzoate.

In another aspect of the present disclosure, which may be combined with any other aspect or embodiment listed herein unless specified otherwise, the composition has one or more of: (i) a clear appearance; (ii) 95.0% to 105.0% of the initial amount of potassium chloride; (iii) a pH of 2.0 to 5.0; (iv) 50% to 150% of the initial amount of sodium benzoate; (v) a total aerobic microbial count of not more than 100 cfu/mL; (vi) a total combined yeast and mold count of not more than 20 cfu/mL; (vii) no *Escherichia coli*; or (viii) no *Burkholderia cepacia* after being subjected to in-use conditions, wherein the in-use conditions comprise: (a) storing the composition at a temperature of about 25° C. and about 60% relative humidity for about 24 months, and then removing 5 aliquots of the composition daily for 6 days; or (b) storing the composition at a temperature of about 25° C. and about 60% relative humidity for about 24 months, and then removing one aliquot of the composition daily for 30 days.

In another aspect of the present disclosure, which may be combined with any other aspect or embodiment listed herein unless specified otherwise, the composition further comprises flavoring.

In another aspect of the present disclosure, which may be combined with any other aspect or embodiment listed herein unless specified otherwise, the composition further comprises colorant.

In another aspect of the present disclosure, which may be combined with any other aspect or embodiment listed herein unless specified otherwise, the composition comprises: about 10% (w/v) potassium chloride; about 1.6% to about 2.6% (w/v) glycerin; about 0.02% to about 0.08% (w/v) sodium benzoate; about 0.05% to about 0.5% (w/v) sucralose; about 0.15% to about 0.35% (w/v) sodium citrate dihydrate; about 0.1% to about 0.25% (w/v) citric acid anhydrous; and water.

In another aspect of the present disclosure, which may be combined with any other aspect or embodiment listed herein unless specified otherwise, the composition comprises: about 20% (w/v) potassium chloride; about 3.6% to about 4.6% glycerin; about 0.05% to about 0.15% (w/v) sodium benzoate; about 0.04% to about 1% (w/v) sucralose; about 0.35% to about 0.8% (w/v) sodium citrate dihydrate; about 0.2% to about 0.45% (w/v) citric acid anhydrous; and water.

In another aspect of the present disclosure, which may be combined with any other aspect or embodiment listed herein unless specified otherwise, the composition comprises: about 10% (w/v) potassium chloride; about 2.1% (w/v) glycerin; about 0.05% (w/v) sodium benzoate; about 0.08% (w/v) sucralose; about 0.26% (w/v) sodium citrate dihydrate; about 0.17% (w/v) citric acid anhydrous; flavoring agent; colorant; and water.

In another aspect of the present disclosure, which may be combined with any other aspect or embodiment listed herein unless specified otherwise, the composition comprises: about 20% (w/v) potassium chloride; about 4.1% (w/v) glycerin; about 0.1% (w/v) sodium benzoate; about 0.15% (w/v) sucralose; about 0.52% (w/v) sodium citrate dihydrate; about 0.34% (w/v) citric acid anhydrous; flavoring agent; colorant; and water.

In another aspect of the present disclosure, which may be combined with any other aspect or embodiment listed herein unless specified otherwise, a method for the treatment of hypokalemia is provided, the method comprising orally administering an aqueous oral composition as disclosed herein to a patient.

In another aspect of the present disclosure, which may be combined with any other aspect or embodiment listed herein unless specified otherwise, administering comprises diluting the composition with a liquid prior to ingestion by the patient.

In another aspect of the present disclosure, which may be combined with any other aspect or embodiment listed herein unless specified otherwise, the method comprises administering about 20 mEq to about 200 mEq potassium per 24 hour period over 2 to 5 divided doses.

In another aspect of the present disclosure, which may be combined with any other aspect or embodiment listed herein unless specified otherwise, the method comprises administering about 40 mEq potassium or less per dose.

Advantageously, the disclosed compositions avoid the use of alcohol preservatives and poorly soluble paraben preservatives while achieving stability upon storage and temperature cycling conditions.

DETAILED DESCRIPTION

Provided herein are stable aqueous oral compositions including potassium chloride. Such compositions can be useful in the treatment of hypokalemia in patients with or without metabolic alkalosis. The compositions can provide advantages over conventional oral liquid compositions containing a bacteriostatic or bactericidal amount of ethanol such as, for example, improved safety for children, particularly very young children. Further, the compositions avoid the use of parabens, which generally have poor aqueous stability.

As used herein, the term "aqueous composition" refers to a composition in which the solvent is wholly or primarily water.

As used herein, the term "solution" refers to liquid compositions in which the solute particles of a substance are dissolved within a solvent. The degree to which a substance dissolves in a solvent to result in a solution is known as solubility.

As used herein, the terms "subject" and "patient" are used interchangeably, and both refer to a recipient on whom a method is conducted according to the present disclosure or another method, as the case may be.

As used herein the term "temperature cycling" includes freeze-thaw cycling and thermal cycling.

As used herein the term "dose" refers to an amount of active agent administered.

As used herein, a w/v % concentration of a solute in an aqueous solution is calculated as follows:

$$\text{Concentration of solute (w/v \%)} = [\text{Mass of Solute (in grams)} / \text{Volume of Solution (in mL)}] \times 100$$

Aqueous Oral Compositions Containing Potassium Chloride:

In one aspect, certain aqueous oral compositions comprising potassium chloride, glycerin, and sodium benzoate are disclosed. Glycerin is a bulking agent and sodium benzoate is a preservative, and these components are present in the aqueous oral compositions in ratios and amounts to provide an unexpectedly stable composition. Certain embodiments of the aqueous oral compositions may include further excipients, including, for example, sweeteners, buffers, colorants, and flavorings, with the balance of the compositions substantially being water. Such aqueous oral compositions may be unexpectedly resistant to formation of precipitates upon storage and/or under stressed conditions such as temperature cycling or exposure to light. In some cases, the aqueous oral compositions have substantially no visible formation of precipitates upon storage and/or under stressed conditions. The phrase "substantially no visible formation of precipitates" refers to the characteristic wherein a solution is essentially devoid of solid particulates upon visible inspection. In certain cases, for example, "substantially no visible formation of precipitates" may mean that the solution does not include precipitates having a particle size of 50 μm or greater. In some cases, the presence of precipitates can be determined by measuring the transmittance of the composition, for example, by comparing the transmittance of the composition after storage or stressed conditions to the initial transmittance of the composition (i.e., before storage and/or exposure to stressed conditions). In certain cases, the transmittance of a composition after storage and/or exposure to stressed conditions is at least 95% of the initial transmittance of composition. In certain embodiments, the transmittance after storage and/or exposure to stressed conditions is at least 96%, at least 97%, at least 98%, at least 99%, at least 99.5%, at least 99.6%, at least 99.7%, at least 99.8%, or at least 99.9% of the initial transmittance. The transmittance can be measured at any suitable wavelength, for example, at 400 nm, at 420 nm, at 440 nm, at 450 nm, at 460 nm, at 480 nm, at 500 nm, at 520 nm, at 540 nm, at 550 nm, at 560 nm, or at 580 nm. Further, in some cases, after storage and/or exposure to stressed conditions, the compositions are unexpectedly resistant to changes in potassium chloride content, sodium benzoate content, pH, and/or microbial levels.

In some embodiments, potassium chloride is present in the composition at a concentration of about 10% to about 20% (w/v) of the aqueous oral composition, or at any value or in any range subsumed therein. In certain embodiments, potassium chloride is present in the composition at a concentration ranging from about 10% to about 18% (w/v), about 10% to about 16% (w/v), about 10% to about 14% (w/v), about 10% to about 12% (w/v), about 12% to about 20% (w/v), about 14% to about 20% (w/v), about 16% to about 20% (w/v), about 18% to about 20% (w/v), about 12% to about 18% (w/v), or about 14% to about 16% (w/v) of the composition. In various embodiments, potassium chloride is present in the composition at a concentration of about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), or about 20% (w/v) of the composition.

In some embodiments, glycerin is present in the composition at a concentration of about 1% to about 5% (w/v) of the aqueous oral composition, or at any value or in any range subsumed therein. In certain embodiments, glycerin is present in the composition at a concentration ranging from about 1% to about 4.5% (w/v), about 1% to about 4% (w/v), about 1% to about 3.5% (w/v), about 1% to about 3% (w/v), about 1% to about 2.5% (w/v), about 1% to about 2% (w/v), about 1% to about 1.5% (w/v), about 1.5% to about 5% (w/v), about 2% to about 5% (w/v), about 2.5% to about 5% (w/v), about 3% to about 5% (w/v), about 3.5% to about 5% (w/v), about 4% to about 5% (w/v), about 4.5% to about 5% (w/v), about 1.5% to about 4.5% (w/v), about 2% to about 4% (w/v), about 2.5% to about 3.5% (w/v), about 1.3% to about 2.9% (w/v), about 1.5% to about 2.7% (w/v), about 1.6% to about 2.6% (w/v), about 1.7% to about 2.5% (w/v), about 1.8% to about 2.4% (w/v), about 1.9% to about 2.3% (w/v), about 2% to about 2.2% (w/v), about 3.2% to about 5% (w/v), about 3.3% to about 4.9% (w/v), about 3.4% to about 4.8% (w/v), about 3.5% to about 4.7% (w/v), about 3.6% to about 4.6% (w/v), about 3.7% to about 4.5% (w/v), about 3.8% to about 4.4% (w/v), about 3.9% to about 4.3% (w/v), or about 4% to about 4.2% (w/v) of the composition. In various embodiments, glycerin is present in the composition at a concentration of about 1% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2% (w/v), about 2.1% (w/v), about 2.2% (w/v), about 2.3% (w/v), about 2.4% (w/v), about 2.5% (w/v), about 2.6% (w/v), about 2.7% (w/v), about 2.8% (w/v), about 2.9% (w/v), about 3% (w/v), about 3.1% (w/v), about 3.2% (w/v), about 3.3% (w/v), about 3.4% (w/v), about 3.5% (w/v), about 3.6% (w/v), about 3.7% (w/v), about 3.8% (w/v), about 3.9% (w/v), about 4% (w/v), about 4.1% (w/v), about 4.2% (w/v), about 4.3% (w/v), about 4.4% (w/v), about 4.5% (w/v), about 4.6% (w/v), about 4.7% (w/v), about 4.8% (w/v), about 4.9% (w/v), or about 5% (w/v) of the composition.

In some embodiments, sodium benzoate is present in the composition in an amount sufficient to provide a stable composition, for example, by providing anti-microbial activity that prevents growth and/or spread of bacteria, yeast, and molds. In some embodiments, sodium benzoate is present in the composition at a concentration of about 0.02% to about 0.2% (w/v) of the composition, or in any concentration or within any concentration range subsumed therein. In certain embodiments, sodium benzoate is present in a concentration ranging from about 0.02% to about 0.18% (w/v), about 0.02% to about 0.16% (w/v), about 0.02% to about 0.15% (w/v), about 0.02% to about 0.14% (w/v), about 0.02% to about 0.12% (w/v), about 0.02% to about 0.1% (w/v), about 0.02% to about 0.08% (w/v), about 0.02% to about 0.06% (w/v), about 0.02% to about 0.05% (w/v), about 0.02% to about 0.04% (w/v), about 0.04% to about 0.2% (w/v), about 0.05% to about 0.2% (w/v), about 0.06% to about 0.2% (w/v), about 0.08% to about 0.2% (w/v), about 0.1% to about 0.2% (w/v), about 0.12% to about 0.2% (w/v), about 0.14% to about 0.2% (w/v), about 0.15% to about 0.2% (w/v), about 0.16% to about 0.2% (w/v), about 0.18% to about 0.2% (w/v), about 0.03% to about 0.07% (w/v), about 0.04% to about 0.06% (w/v), about 0.05% to about 0.15% (w/v), about 0.06% to about 0.14% (w/v), about 0.07% to about 0.13% (w/v), about 0.08% to about 0.12% (w/v), or about 0.09% to about 0.11% (w/v) of the composition. In various embodiments, sodium benzoate is present in a concentration of about 0.02% (w/v), about 0.04% (w/v), about 0.05% (w/v), about 0.06% (w/v), about 0.08% (w/v), about 0.1% (w/v), about 1.2% (w/v), about 1.4% (w/v), about 1.5% (w/v), about 1.6% (w/v), about 1.7% (w/v), about 1.8% (w/v), about 1.9% (w/v), or about 0.2% (w/v) of the composition.

In some embodiments, a buffer is included in the composition in an amount sufficient to maintain a desired pH of the composition. Suitable buffers for inclusion in the compositions include, but are not limited to, citric acid, citrate salts (e.g., sodium, potassium, or magnesium citrate), acetic acid, acetate salts (e.g., sodium, potassium, or magnesium acetate), bicarbonate salts (e.g., sodium, potassium, or magnesium bicarbonate), lactic acid, lactate salts (e.g., sodium, potassium, or magnesium lactate), gluconic acid, gluconate salts (e.g., sodium, potassium, or magnesium gluconate), carbonate salts (e.g., sodium, potassium, or magnesium carbonate), tartaric acid, tartrate salts (e.g., sodium, potassium, or magnesium, tartrate), phosphate salts (e.g., disodium hydrogenphosphate, dipotassium hydrogenphosphate, dimagnesium hydrogenphosphate, trisodium phosphate, tripotassium phosphate, trimagnesium phosphate), polyphosphate salts, pyrophosphate salts, and mixtures thereof.

In some embodiments, the buffer is a mixture of citric acid and sodium citrate. In various embodiments, the sodium citrate can include hydrates, solvates, or anhydrous forms thereof. In various embodiments, the sodium citrate can be or can include sodium citrate dihydrate. In some embodiments, sodium citrate dihydrate is present in the composition in a concentration of 0.1% to about 1% (w/v) of the composition, or in any concentration or within any concentration range subsumed therein. In certain embodiments, sodium citrate dihydrate is present in the composition in a concentration of about 0.1% to about 0.5% (w/v), about 0.1% to about 0.4% (w/v), about 0.15% to about 0.35% (w/v), about 0.2% to about 0.3% (w/v), about 0.3% to about 1% (w/v), about 0.35% to about 0.8% (w/v), or about 0.4% to about 0.6% (w/v) of the composition. In various embodiments, sodium citrate dihydrate is present in the composition in a concentration of about 0.1% (w/v), about 0.15% (w/v), about 0.2% (w/v), about 0.25% (w/v), about 0.26% (w/v), about 0.3% (w/v), about 0.35% (w/v), about 0.4% (w/v), about 0.45% (w/v), about 0.5% (w/v), about 0.52% (w/v), about 0.55% (w/v), about 0.6% (w/v), about 0.65% (w/v), about 0.7% (w/v), about 0.75% (w/v), about 0.8% (w/v), about 0.85% (w/v), about 0.9% (w/v), about 0.95% (w/v), or about 1% (w/v) of the composition.

In some embodiments, citric acid is present in the composition in a concentration of about 0.05% to about 0.8% (w/v) of the composition, or in any concentration or within any concentration range subsumed therein. In certain embodiments, citric acid is present in the composition in a concentration of about 0.05% to about 0.3% (w/v), about 0.08% to about 0.28% (w/v), about 0.1% to about 0.25% (w/v), about 0.15% to about 0.2% (w/v), about 0.15% to about 0.5% (w/v), about 0.2% to about 0.45% (w/v), about 0.25% to about 0.4% (w/v), or about 0.3% to about 0.38% (w/v) of the composition. In various embodiments citric acid is present in the composition in a concentration of about 0.05% (w/v), about 0.1% (w/v), about 0.15% (w/v), about 0.17% (w/v), about 0.2% (w/v), about 0.25% (w/v), about 0.3% (w/v), about 0.34% (w/v), about 0.35% (w/v), about 0.4% (w/v), about 0.45% (w/v), about 0.5% (w/v), about 0.55% (w/v), about 0.6% (w/v), about 0.65% (w/v), about 0.7% (w/v), about 0.75% (w/v), or about 0.8% (w/v) of the composition.

In some embodiments, the buffer is selected such that the composition has a pH of about 2 to about 5, or at any value or in any range subsumed therein. In some embodiments, the composition has a pH ranging from about 2 to about 5, about 2.5 to about 5, about 3 to about 5, or about 3.5 to about 4.5. In certain embodiments, the composition has a pH of about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, or about 5.

In some embodiments, the composition can comprise one or more additional excipients, including but not limited to, sweeteners, flavoring agents, coloring agents, and the like.

One or more sweeteners can be used in the composition and can include any compound or compounds that provide a sweet taste, including, for example, natural and synthetic sugars, natural and artificial sweeteners, natural extracts, and any material that initiates a sweet sensation in a subject. In some embodiments, the compositions disclosed herein comprise one or more sweeteners. In some embodiments, solid, powder sweeteners are included in the composition disclosed herein. In some embodiments, sweeteners in liquid form, also referred to as syrups, are included in the compositions disclosed herein.

Suitable sweeteners for inclusion in the compositions include, but are not limited to, glucose, fructose, sucrose, xylitol, tagatose, sucralose, maltitol, isomaltulose, ISOMALT™ (hydrogenated isomaltulose), lactitol, sorbitol, erythritol, trehalose, maltodextrin, polydextrose, and the like. Other sweeteners that may be included in the compositions herein include, for example, glycerin, inulin, erythritol, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, etc., and/or as branded products, e.g., SWEET AM™ liquid (Product Code 918.003-propylene glycol, ethyl alcohol, and proprietary artificial flavor combination, Flavors of North America) and SWEET AM™ powder (Product Code 918.005—maltodextrin, sorbitol, and fructose combination and Product Code 918.010—water, propylene glycol, sorbitol, fructose, and proprietary natural and artificial flavor combination, Flavors of North America), PROSWEET™ (1-10% proprietary plant/vegetable extract and 90-99% dextrose combination, Virginia Dare), MALTISWEET™ (maltitol solution, Ingredion), SORBO™ (sorbitol and sorbitol/xylitol solution, SPI Polyols), INVERTOSE™ (high fructose corn syrup, Ingredion), REBALANCE™ M60 and X60 (sucralose and maltodextrin, Tate and Lyle), and ORA-SWEET® sugar-free flavored syrup (Paddock Laboratories, Inc.). Sweeteners can be used singularly or in combinations of two or more. Suitable concentrations of different sweeteners can be selected based on published information, manufacturers' data sheets, and by routine testing.

In some embodiments, the sweetener is present in the composition in a concentration of about 0.01% to about 5% (w/v) of the composition, or in any concentration or within any concentration range subsumed therein. In certain embodiments, the sweetener is present in the composition in a concentration ranging from about 0.02% to about 2.5% (w/v), about 0.04% to about 1% (w/v), about 0.05% to about 0.5% (w/v), about 0.06% to about 0.2% (w/v), or about 0.08% to about 0.15% (w/v) of the composition.

In some embodiments, the sweetener comprises sucralose. In certain embodiments, sucralose is present in the composition at a concentration of about 0.02% to about 0.3% (w/v) of the composition, or in any concentration or within any concentration range subsumed therein. In certain embodiments, sucralose is present in the composition at a concentration of about 0.02% to about 0.2% (w/v), about 0.04% to about 0.16% (w/v), about 0.06% to about 0.12% (w/v), about 0.08% to about 0.1% (w/v), about 0.05% to about 0.25% (w/v), about 0.08% to about 0.2% (w/v), about 0.1% to about 0.18% (w/v), or about 0.12% to about 0.16% (w/v) of the composition. In various embodiments, sucralose is present in the composition at a concentration of about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.1% (w/v), about 0.11% (w/v), about 0.12% (w/v), about 0.13% (w/v), about 0.14% (w/v), about 0.15% (w/v), about 0.16% (w/v), about 0.17% (w/v), about 0.18% (w/v), about 0.19% (w/v), or about 0.2% (w/v).

One or more flavoring agents can be used to enhance the taste or aroma of the composition. Suitable natural or synthetic flavoring agents can be used, non-limiting examples of which include almond, anise, apple, apricot, bergamot, blackberry, blackcurrant, blueberry, bubblegum, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, tutti-frutti, vanilla, wintergreen, and the like. In certain embodiments, the flavoring agent comprises an orange flavoring agent.

In some embodiments, the flavoring agent is present in a concentration of about 0.05% to about 2% (w/v) of the composition, or in any concentration or within any concentration range subsumed therein. In certain embodiments, the flavoring agent is present in a concentration ranging from about 0.1% to about 0.5% (w/v), about 0.15% to about 0.45% (w/v), about 0.2% to about 0.4% (w/v), about 0.15% to about 0.35% (w/v), about 0.4% to about 0.8% (w/v), about 0.45% to about 0.75% (w/v), or about 0.5% to about 0.7% (w/v) of the composition. In various embodiments, the flavoring agent is present in a concentration of about 0.05% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 1.2% (w/v), about 1.4% (w/v), about 1.5% (w/v), about 1.8% (w/v), or about 2% (w/v).

Colorants can be included in the compositions herein for identification and/or aesthetic purposes. Suitable colorants include, but are not limited to, FD&C Red No. 3, FD&C Red No. 20, FD&C Red No. 40, FD&C Yellow No. 6, FD&C Blue No. 2, FD&C Green No. 5, FD&C Orange No. 5, caramel, ferric oxide, and mixtures of any two or more thereof.

In some embodiments, the composition is free of alcohol (i.e., ethanol). A composition that is free of alcohol has essentially no detectable level of alcohol, for example, the concentration of alcohol in the composition is less than 0.1% (w/v), less than 0.05% (w/v), less than 0.02% (w/v), or less than 0.01% (w/v) of the composition.

In some embodiments, the composition is free of parabens, such as methylparaben, ethylparaben, propylparaben, butylparaben, and/or heptylparaben. A composition that is free of parabens has no added parabens and has essentially no detectable level of parabens, for example, the concentration of parabens is less than 0.1% (w/v), less than 0.05% (w/v), less than 0.02% (w/v), or less than 0.01% (w/v) of the composition.

The aqueous oral compositions disclosed herein are in the form of a solution, which advantageously provides a clear product without visible precipitates or particulate matter. Surprisingly and unexpectedly, the compositions are stable and remain in solution under storage or stressed conditions, such as freeze-thaw cycling or exposure to light. In some embodiments, the compositions have no visible formation of precipitates after being subjected to one, two, or three freeze-thaw cycles. In certain embodiments, a freeze-thaw cycle comprises maintaining the composition in a frozen state by placing the composition at a temperature below 0° C. for a period of time, followed by allowing the composition to return to a thawed state by placing the composition at a temperature above 0° C. for a period of time. In some embodiments, the temperature for maintaining the composition in a frozen state is about −20° C. to about 0° C., about −20° C. to about −5° C., about −20° C. to about −10° C., below −5° C., below −10° C., or below −15° C. In some embodiments, the temperature for maintaining the composition in a thawed state is about 2° C. to about 8° C., about 15° C. to about 30° C., about 20° C. to about 25° C., about 35° C. to about 40° C., above 2° C., above 5° C., above 10° C., above 15° C., above 20° C., above 25° C., above 30° C., or above 35° C. In various embodiments, the composition is maintained in a frozen state for about 1 to about 30 days, about 1 to about 20 days, about 1 to about 14 days, about 1 to about 7 days, or about 2 to about 5 days. In various embodiments, the composition is maintained in a thawed state for about 1 to about 30 days, about 1 to about 20 days, about 1 to about 14 days, about 1 to about 7 days, or about 2 to about 5 days. In various embodiments, a freeze-thaw cycle comprises: (i) maintaining the composition at a temperature of about −20° C. to about −10° C. for about two days; followed by (ii) maintaining the composition at a temperature of about 40° C. for about two days. In various embodiments, a freeze-thaw cycle comprises: (i) maintaining the composition at a temperature of about −20° C. to about −10° C. for about two days; followed by (ii) maintaining the composition at a temperature of about 25° C. for about two days.

In some embodiments, the compositions have no visible formation of precipitates after being subjected to one, two, or three thermal cycles. In certain embodiments, a thermal cycle comprises maintaining the composition in a cooled state by placing the composition at a temperature below room temperature for a period of time, followed by allowing the composition to return to a warmed state by placing the composition at a temperature at or above room temperature for a period of time. In some embodiments, the temperature for maintaining the composition in a cooled state is about 2° C. to about 8° C., about 2° C. to about 6° C., or about 2° C. to about 4° C. In some embodiments, the temperature for maintaining the composition in a warmed state is about 23° C. to about 27° C., about 20° C. to about 25° C., about 25° C. to about 30° C., about 30° C. to about 35° C., about 35° C. to about 40° C., about 40° C. to about 45° C., about 38° C. to about 42° C., above 20° C., above 25° C., above 30° C., or above 35° C. In various embodiments, the composition is maintained in a cooled state for about 1 to about 30 days, about 1 to about 20 days, about 1 to about 14 days, about 1 to about 7 days, or about 2 to about 5 days. In various embodiments, the composition is maintained in a warmed state for about 1 to about 30 days, about 1 to about 20 days, about 1 to about 14 days, about 1 to about 7 days, or about 2 to about 5 days. In various embodiments, a thermal cycle comprises: (i) maintaining the composition at a temperature of about 2° C. to about 8° C. for about two days; followed by (ii) maintaining the composition at a temperature of about 40° C. for about two days. In various embodiments, a thermal cycle comprises: (i) maintaining the composition at a temperature of about 2° C. to about 8° C. for about two days; followed by (ii) maintaining the composition at a temperature of about 25° C. for about two days In some embodiments, the compositions have no visible formation of precipitates after exposure to light. In various embodiments, the compositions have no visible formation of precipitates after exposure to cool white fluorescent light, near ultraviolet light, or combinations thereof. In certain embodiments, the light exposure is cool white fluorescent light for about 1.2 million lux hours, followed by near ultraviolet light for 200 watt hours/square meter. In some embodiments, the composition contains an initial amount of potassium chloride, and after exposure of the composition to cool white fluorescent light for about 1.2 million lux hours, followed by exposure to near ultraviolet light for about 200 watt hours/square meter to obtain a light-treated composition, the light-treated composition contains potassium chloride in an amount that is no more than 3% different from the initial amount of potassium chloride. In some embodiments, the composition contains an initial amount of sodium benzoate, and after exposure of the composition to cool white fluorescent light for about 1.2 million lux hours, followed by exposure to near ultraviolet light for about 200 watt hours/square meter to obtain a light-treated composition, the light-treated composition contains sodium benzoate in an amount that is no more than 5% different from the initial amount of sodium benzoate.

Methods of Treatment:

In another aspect, methods of treatment comprising administering an aqueous oral composition disclosed herein to a subject in need thereof are provided. In some embodiments, an aqueous oral composition as disclosed herein can be used to treat hypokalemia in a subject. The subject can be a pediatric subject, an adult subject, or a geriatric subject.

Dosing:

Dosages of the compositions disclosed herein can be determined by any suitable method. In various embodiments, the dosage of potassium for treating hypokalemia in adults is about 20 mEq to about 200 mEq potassium per 24 hour period. In certain embodiments of a method according to the present disclosure, the dosage of potassium administered to a subject is about 20 mEq to about 150 mEq potassium, about 20 mEq to about 100 mEq potassium, about 20 mEq to about 50 mEq potassium, about 20 mEq to about 40 mEq potassium, about 40 mEq to about 100 mEq potassium, or about 40 mEq to about 60 mEq potassium per 24 hour period. In various embodiments, the daily dose is administered over 2 to 5 divided doses, 2 to 4 divided doses, 2 to 3 divided doses, 2 divided doses, 3 divided doses, 4 divided doses, or 5 divided doses. In various embodiments, about 40 mEq potassium or less is administered per dose. In certain embodiments, about 40 mEq potassium, about 30 mEq potassium, about 20 mEq potassium, about 10 mEq potassium, about 5 mEq potassium, or about 4 mEq potassium is administered per dose.

In various embodiments of a method according to the present disclosure, the dosage of potassium administered to a subject for treating hypokalemia in pediatric patients is about 1 mEq/kg to about 4 mEq/kg potassium per 24 hour period. In some embodiments, the dosage of potassium is about 2 mEq/kg to about 4 mEq/kg potassium, or about 2 mEq/kg to about 3 mEq/kg potassium per 24 hour period. In certain embodiments, the dosage of potassium is 100 mEq or less, 90 mEq or less, 80 mEq or less, 70 mEq or less, 60 mEq or less, 50 mEq or less, 40 mEq or less, 30 mEq or less, or 20 mEq or less per 24 hour period. In various embodiments, the daily dose is administered over 2 to 5 divided doses, 2 to 4 divided doses, 2 to 3 divided doses, 2 divided doses, 3 divided doses, 4 divided doses, or 5 divided doses. In various embodiments, about 1 mEq/kg potassium or less is administered per dose. In various embodiments, about 40 mEq potassium or less is administered per dose. In certain embodiments, about 40 mEq potassium, about 30 mEq potassium, about 20 mEq potassium, about 10 mEq potassium, about 5 mEq potassium, or about 4 mEq potassium is administered per dose.

Administration:

The compositions disclosed herein can be administered at a dosage described herein or at other appropriate dose levels contemplated by a medical practitioner. In certain embodiments, the compositions described herein are administered for prophylactic and/or therapeutic treatments. In certain therapeutic applications, the compositions are administered to a patient already suffering from a condition, e.g., hypokalemia, in an amount sufficient to cure the condition or at least partially arrest or ameliorate the symptoms, e.g., increase potassium levels. Amounts effective for this use depend on the severity of the condition, previous therapy, the patient's health status, weight, and response to the oral potassium compositions, and the judgment of the treating physician. Therapeutically effective amounts are optionally determined by methods including, but not limited to, a dose escalation clinical trial.

In certain embodiments wherein the patient's condition does not improve, upon the doctor's discretion, the compositions described herein may be administered chronically, that is, for an extended period of time, including throughout the duration of the patient's life, in order to ameliorate or otherwise control or limit the symptoms of the patient's condition. In other embodiments, administration of the composition continues until complete or partial response of a condition occurs.

In some embodiments, the compositions disclosed herein are diluted with a liquid prior to ingestion by the patient. In various embodiments, the compositions are diluted in water or juice. In certain embodiments, the compositions are diluted in a ratio of 1 part composition to 40 parts diluent, 1 part composition to 30 parts diluent, 1 part composition to 25 parts diluent, 1 part composition to 20 parts diluent, 1 part composition to 15 parts diluent, 1 part composition to 10 parts diluent, 1 part composition to 8 parts diluent, 1 part composition to 7 parts diluent, 1 part composition to 6 parts diluent, 1 part composition to 5 parts diluent, 1 part composition to 4 parts diluent, 1 part composition to 3 parts diluent, or 1 part composition to 2 parts diluent.

In some embodiments, the compositions according to the present disclosure are administered to a subject who is in a fed state. A fed state refers to a subject who has taken food or has had a meal. In certain embodiments, the composition is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In certain embodiments, the composition is administered to a subject with food.

EXAMPLES

Example 1. Preparation of an Aqueous Oral Composition Including Potassium Chloride Two aqueous oral compositions were prepared using the method described below. The formulations of the compositions are shown in Tables 1 and 2 below. Unless otherwise noted, all components were added in the quantities needed to obtain the concentrations provided in Tables 1 and 2.

To prepare the compositions, the required amounts of glycerin and purified water were mixed in a stainless steel mixing tank. With the mixer running, the required amount of sodium benzoate was added to the mixing tank. With the mixer running, the required amounts of sucralose, sodium citrate dihydrate, and anhydrous citric acid were added to the mixing tank and mixing was continued for 15 to 20 minutes. With the mixer running, the required amount of potassium chloride was added to the mixing tank and mixing was continued for 30 to 35 minutes. With the mixer running, the required amount of natural and artificial orange flavor was added to the mixing tank. With the mixer running, the required amount of FD&C Yellow #6 was added to the mixing tank and mixing was continued for 30 to 35 minutes. The resulting batch was then filtered through 5 μm filters into a clean stainless steel holding tank, after which the filtered bulk product was packaged into bottles and/or unit dose cups.

TABLE 1

Aqueous Oral Composition Including 20 mEq/15 mL Potassium Chloride.

| Component | mg/15 mL | % (w/v) | Function |
|---|---|---|---|
| Potassium Chloride, USP | 1500.00 | 10.000 | Active Ingredient |
| Glycerin, USP | 310.00 | 2.067 | Bulking |
| Sodium Benzoate, NF | 7.50 | 0.050 | Preservative |
| Sucralose, NF | 11.250 | 0.075 | Sweetener |
| Sodium Citrate Dihydrate, USP | 39.150 | 0.261 | Buffer |
| Citric Acid, Anhydrous, USP | 25.450 | 0.170 | Buffer |
| Natural and Artificial Orange Flavor | 45.000 | 0.300 | Flavoring |
| FD&C Yellow #6 | 0.938 | 0.00625 | Colorant |
| Purified Water, USP | 14,050.715 | 93.671 | Vehicle |

TABLE 2

Aqueous Oral Composition Including 40 mEq/15 mL Potassium Chloride.

| Component | mg/15 mL | % (w/v) | Function |
|---|---|---|---|
| Potassium Chloride, USP | 3000.00 | 20.000 | Active Ingredient |
| Glycerin, USP | 620.00 | 4.1330 | Bulking |
| Sodium Benzoate, NF | 15.00 | 0.1000 | Preservative |
| Sucralose, NF | 22.50 | 0.1500 | Sweetener |
| Sodium Citrate Dihydrate, USP | 78.3 | 0.5220 | Buffer |
| Citric Acid, Anhydrous, USP | 50.90 | 0.3393 | Buffer |
| Natural and Artificial Orange Flavor | 90.00 | 0.6000 | Flavoring |
| FD&C Yellow #6 | 1.875 | 0.0125 | Colorant |
| Purified Water, USP | 13,097.475 | 87.3165 | Vehicle |

Example 2. Freeze-Thaw/Thermal Cycling Study of Oral Composition Including 20 mEq/15 mL Potassium Chloride For purposes of conducting a freeze-thaw/thermal cycling study, the oral composition including 20 mEq/15 mL potassium chloride samples of Example 1 were packaged in High Density Polyethylene ("HDPE") bottles. The bottles were segregated into packs and placed in freezing conditions, followed by thaw conditions, as described in the table below, for one, two, or three cycles.

TABLE 3

Conditions for freeze-thaw/thermal cycling study.

| Study | Condition | Cycle 1 | Cycle 2 | Cycle 3 |
|---|---|---|---|---|
| 1 | −20° C. to −10° C. | 2 days | 2 days | 2 days |
| | 40° C. ± 2° C./75% ± 5% relative humidity (RH) | 2 days | 2 days | 2 days |
| 2 | 2° C. to 8° C. | 2 days | 2 days | 2 days |
| | 40° C. ± 2° C./75% ± 5% RH | 2 days | 2 days | 2 days |

TABLE 3-continued

Conditions for freeze-thaw/thermal cycling study.

| Study | Condition | Cycle 1 | Cycle 2 | Cycle 3 |
|---|---|---|---|---|
| 3 | −20° C. to −10° C. | 2 days | 2 days | 2 days |
| | 25° C. ± 2° C./60% ± 5% RH | 2 days | 2 days | 2 days |
| 4 | 2° C. to 8° C. | 2 days | 2 days | 2 days |
| | 25° C. ± 2° C./60% ± 5% RH | 2 days | 2 days | 2 days |

Samples that had undergone three freeze-thaw cycles were analyzed for appearance, container/closure, assay, pH, preservative content, and microbial limits. These samples upon testing met all specifications as described in the tables below.

TABLE 4

Study 1 (−20° C. to −10° C./40° C. ± 2° C./75% ± 5% RH) Oral Composition Including 20 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 100.3% |
| pH | 2.0-5.0 | | 4.2 |
| Preservative Content | Sodium Benzoate | 0.025% w/v-0.075% w/v | 0.048% |
| | | 50%-150% (% labeled amount) | 97% |
| Microbial Limits | Total Aerobic Microbial Count | NMT (not more than) 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 5

Study 2 (2° C. to 8° C./40° C. ± 2° C./75% ± 5% RH) Oral Composition Including 20 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 99.6% |
| pH | 2.0-5.0 | | 4.2 |
| Preservative Content | Sodium Benzoate | 0.025% w/v-0.075% w/v | 0.049% |
| | | 50%-150% (% labeled amount) | 98% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 6

Study 3 (−20° C. to −10° C./25° C. ± 2° C./60% ± 5% RH) Oral Composition Including 20 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 99.4% |
| pH | 2.0-5.0 | | 4.2 |
| Preservative Content | Sodium Benzoate | 0.025% w/v-0.075% w/v | 0.049% |
| | | 50%-150% (% labeled amount) | 98% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 7

Study 4 (2° C. to 8° C./25° C. ± 2° C./60% ± 5% RH) Oral Composition Including 20 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 99.8% |
| pH | 2.0-5.0 | | 4.2 |
| Preservative Content | Sodium Benzoate | 0.025% w/v-0.075% w/v | 0.049% |
| | | 50%-150% (% labeled amount) | 99% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

As described in the tables above, the oral composition including 20 mEq/15 mL potassium chloride and its associated container/closure were not adversely affected by the tested freeze-thaw conditions, and were not adversely affected by short term storage excursions outside recommended storage conditions likely to be encountered during product distribution.

Example 3. Freeze-Thaw/Thermal Cycling Study of Oral Composition Including 40 mEq/15 mL Potassium Chloride For purposes of conducting a freeze-thaw/thermal cycling study, the oral composition including 40 mEq/15 mL potassium chloride samples of Example 1 were packaged in High Density Polyethylene ("HDPE") bottles. The bottles were segregated into packs and placed in freezing conditions, followed by thaw conditions, as described in the table below, for one, two, or three cycles.

TABLE 8

Conditions for freeze-thaw/thermal cycling study.

| Study | Condition | Cycle 1 | Cycle 2 | Cycle 3 |
|---|---|---|---|---|
| 1 | −20° C. to −10° C. | 2 days | 2 days | 2 days |
| | 40° C. ± 2° C./75% ± 5% RH | 2 days | 2 days | 2 days |
| 2 | 2° C. to 8° C. | 2 days | 2 days | 2 days |
| | 40° C. ± 2° C./75% ± 5% RH | 2 days | 2 days | 2 days |
| 3 | −20° C. to −10° C. | 2 days | 2 days | 2 days |
| | 25° C. ± 2° C./60% ± 5% RH | 2 days | 2 days | 2 days |
| 4 | 2° C. to 8° C. | 2 days | 2 days | 2 days |
| | 25° C. ± 2° C./60% ± 5% RH | 2 days | 2 days | 2 days |

Samples that had undergone three freeze-thaw cycles were analyzed for appearance, container/closure, assay, pH, preservative content, and microbial limits. These samples upon testing met all specifications as described in the tables below.

TABLE 9

Study 1 (−20° C. to −10° C./40° C. ± 2° C./75% ± 5% RH) Oral Composition Including 40 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 100.5% |
| pH | 2.0-5.0 | | 4.2 |
| Preservative Content | Sodium Benzoate | 0.050% w/v-0.150% w/v | 0.093% |
| | | 50%-150% (% labeled amount) | 93% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 10

Study 2 (2° C. to 8° C./40° C. ± 2° C./75% ± 5% RH) Oral Composition Including 40 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 100.0% |
| pH | 2.0-5.0 | | 4.2 |
| Preservative Content | Sodium Benzoate | 0.050% w/v-0.150% w/v | 0.098% |
| | | 50%-150% (% labeled amount) | 98% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 11

Study 3 (−20° C. to −10° C./25° C. ± 2° C./60% ± 5% RH) Oral Composition Including 40 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 100.1% |
| pH | 2.0-5.0 | | 4.2 |
| Preservative Content | Sodium Benzoate | 0.050% w/v-0.150% w/v | 0.098% |
| | | 50%-150% (% labeled amount) | 98% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 12

Study 4 (2° C. to 8° C./25° C. ± 2° C./60% ± 5% RH) Oral Composition Including 40 mEq/15 mL Potassium Chloride.

| Test | Specification | | Results After 3 Freeze-Thaw Cycles |
|---|---|---|---|
| Appearance | Clear orange liquid | | Conforms |
| Container/ Closure | No damage to the container closure and no leakage of the product indicated | | Conforms |
| Assay | 95.0%-105.0% of the label amount of Potassium Chloride | | 98.8% |
| pH | 2.0-5.0 | | 4.1 |
| Preservative Content | Sodium Benzoate | 0.050% w/v-0.150% w/v | 0.099% |
| | | 50%-150% (% labeled amount) | 99% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

As described in the tables above, the oral composition including 40 mEq/15 mL potassium chloride and its associated container/closure were not adversely affected by the tested freeze-thaw conditions, and were not adversely affected by short term storage excursions outside recommended storage conditions likely to be encountered during product distribution.

Example 4. Photostability Study of Oral Compositions Including 20 mEq/15 mL and 40 mEq/15 mL Potassium Chloride For purposes of conducting a photostability study, the oral compositions including 20 mEq/15 mL and 40 mEq/15 mL potassium chloride of Example 1 were placed in clear glass bottles (for direct exposure samples) or were maintained as finished product samples (for primary package samples) in high density polyethylene bottles. A dark control sample was obtained by wrapping the sample in at least three layers of aluminum foil. The samples were exposed to cool white fluorescent light for at least 1.2 million lux hours followed by near ultra violet light for 200 watt hours/square meter in a photostability chamber. After exposure, the samples were analyzed for appearance, assay of potassium chloride by potentiometric titration, and sodium benzoate content, and the results are provided in the tables below.

TABLE 13

Appearance of Oral Compositions Including 20 mEq/15 mL or 40 mEq/15 mL Potassium Chloride During Photostability Study.

| Packaging | Strength | Sample | Appearance |
|---|---|---|---|
| 1 Gallon Jug | 20 mEq/15 mL | Initial | Clear orange liquid |
| | | Primary package | Clear orange liquid |
| | | Direct exposure | Clear orange liquid |
| | | Dark control | Clear orange liquid |
| 16 oz Bottle | 20 mEq/15 mL | Initial | Clear orange liquid |
| | | Direct exposure | Clear orange liquid |
| | | Primary package | Clear orange liquid |
| | | Dark control | Clear orange liquid |
| 16 oz Bottle | 40 mEq/15 mL | Initial | Clear orange liquid |
| | | Direct exposure | Clear orange liquid |
| | | Primary package | Clear orange liquid |
| | | Dark control | Clear orange liquid |

No changes were observed in the physical appearance of any of the tested samples during the entire photostability study.

TABLE 14

Assay of Potassium Chloride of Oral Compositions Including 20 mEq/15 mL or 40 mEq/15 mL Potassium Chloride During Photostability Study.

| Packaging | Strength | Sample | % Assay | % Difference |
|---|---|---|---|---|
| 1 Gallon Jug | 20 mEq/15 mL | Initial | 99.7 | NA |
| | | Primary package | 99.6 | 0.1 |
| | | Direct exposure | 100.3 | 0.6 |
| | | Dark control | 100.3 | 0.6 |
| 16 oz Bottle | 20 mEq/15 mL | Initial | 100.7 | NA |
| | | Direct exposure | 99.7 | 1.0 |
| | | Primary package | 100.2 | 0.5 |
| | | Dark control | 102.0 | 1.3 |
| 16 oz Bottle | 40 mEq/15 mL | Initial | 101.6 | NA |
| | | Direct exposure | 99.6 | 2.0 |
| | | Primary package | 99.8 | 1.8 |
| | | Dark control | 99.9 | 1.7 |

The results for % Assay are within the acceptance criterion of 95.0% to 105.0% for all samples, and the % Difference as compared with the initial samples is also within the acceptance criterion of NMT 3.0% for all samples. The % Difference is calculated as the absolute value of the initial % Assay value minus the sample % Assay value for each photostability condition.

TABLE 15

Sodium Benzoate Content of Oral Compositions Including 20 mEq/15 mL or 40 mEq/15 mL Potassium Chloride During Photostability Study.

| | | | % Sodium Benzoate | | | |
|---|---|---|---|---|---|---|
| Packaging | Strength | Sample | % w/v | % Difference | Purity Angle | Purity Threshold |
| 1 Gallon Jug | 20 mEq/15 mL | Initial | 0.05065 | NA | 0.053 | 0.256 |
| | | Primary package | 0.05062 | 0.1 | 0.051 | 0.243 |

TABLE 15-continued

Sodium Benzoate Content of Oral Compositions Including 20 mEq/15 mL or 40 mEq/15 mL Potassium Chloride During Photostability Study.

| | | | % Sodium Benzoate | | | |
|---|---|---|---|---|---|---|
| Packaging | Strength | Sample | % w/v | % Difference | Purity Angle | Purity Threshold |
| | | Dark control | 0.05057 | 0.2 | 0.056 | 0.230 |
| | | Direct exposure | 0.05066 | 0.0 | 0.041 | 0.233 |
| 16 oz Bottle | 20 mEq/15 mL | Initial | 0.05052 | NA | 0.046 | 0.240 |
| | | Direct exposure | 0.05074 | 0.4 | 0.087 | 0.261 |
| | | Primary package | 0.05070 | 0.4 | 0.062 | 0.260 |
| | | Dark control | 0.05052 | 0.0 | 0.048 | 0.236 |
| 16 oz Bottle | 40 mEq/15 mL | Initial | 0.09990 | NA | 0.040 | 0.256 |
| | | Direct exposure | 0.09940 | 0.5 | 0.036 | 0.232 |
| | | Primary package | 0.10029 | 0.4 | 0.065 | 0.257 |
| | | Dark control | 0.09999 | 0.1 | 0.048 | 0.230 |

The results of the sodium benzoate content analysis are within the acceptance criterion of 0.025% w/v to 0.075% w/v for all 20 mEq/15 mL strength samples, and 0.050% w/v to 0.0150% w/v for all 40 mEq/15 mL strength samples. The % Difference as compared with the initial samples is also within the acceptance criterion of NMT 5.0% for all samples. Further, the peak purity meets the requirement for the peak purity criterion (purity angle less than purity threshold) for the sodium benzoate peak, in the control (initial), and in each exposed sample. The purity angle is a measure of the spectral heterogeneity of a peak based on comparison of spectra over all the peak, and the purity threshold is a measure of non-ideal effects.

The studies demonstrate that the oral compositions including 20 mEq/15 mL or 40 mEq/15 mL potassium chloride are photostable when directly exposed to light or when exposed to light in packaging.

Example 5. In-use Stability Study of Oral Compositions Including 20 mEq/15 mL and 40 mEq/15 mL Potassium Chloride For purposes of conducting an in-use stability study, the oral compositions including 20 mEq/15 mL and 40 mEq/15 mL potassium chloride of Example 1 are packaged in 16 oz., white, high density polyethylene bottles with a CRC heat induction seal closure. For an Acute Dose study, the samples were stored inverted at 25° C.±2° C./60%±5% RH for zero months (T0) and twenty-four months (T24), and then five 15 mL aliquots of the oral solution were withdrawn from the samples daily for 6 days. For a Maintenance Dose study, the samples were stored inverted at 25° C.±2° C./60%=5% RH for zero months (To) and twenty-four months (T24), and then one 15 mL aliquot of the oral solution was withdrawn from the samples daily for 30 days.

Following the aliquot withdrawal, for the acute and maintenance dosing periods, the oral solution remaining in the bottles was mixed to form a composite sample that was analyzed for appearance, assay, pH, preservative content, and microbial limits. These samples upon testing met all specifications as described in the tables below.

TABLE 16

Acute Dosing In-Use Stability Study for Oral Composition Including 20 mEq/15 mL Potassium Chloride.

| Test | Specification | | Results |
|---|---|---|---|
| Appearance | Clear orange liquid | | Conforms |
| Assay | 95.0%-105.0% of the label amount of Potassium Chloride | | 100.4% |
| pH | 2.0-5.0 | | 4.2 |
| Preservative Content | Sodium Benzoate | 0.025% w/v-0.075% w/v | 0.049% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 17

Maintenance Dosing In-Use Stability Study for Oral Composition Including 20 mEq/15 mL Potassium Chloride.

| Test | Specification | | Results |
|---|---|---|---|
| Appearance | Clear orange liquid | | Conforms |
| Assay | 95.0%-105.0% of the label amount of Potassium Chloride | | 100.4% |
| pH | 2.0-5.0 | | 4.3 |
| Preservative Content | Sodium Benzoate | 0.025% w/v-0.075% w/v | 0.051% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 18

Acute Dosing In-Use Stability Study for Oral Composition Including 40 mEq/15 mL Potassium Chloride.

| Test | Specification | | Results |
|---|---|---|---|
| Appearance | Clear orange liquid | | Conforms |
| Assay | 95.0%-105.0% of the label amount of Potassium Chloride | | 100.0% |
| pH | 2.0-5.0 | | 4.2 |
| Preservative Content | Sodium Benzoate | 0.050% w/v-0.150% w/v | 0.100% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

TABLE 19

Maintenance Dosing In-Use Stability Study for Oral Composition Including 40 mEq/15 mL Potassium Chloride.

| Test | Specification | Results |
|---|---|---|
| Appearance | Clear orange liquid | Conforms |
| Assay | 95.0%-105.0% of the label amount of Potassium Chloride | 100.5% |

TABLE 19-continued

Maintenance Dosing In-Use Stability Study for Oral Composition Including 40 mEq/15 mL Potassium Chloride.

| Test | Specification | | Results |
|---|---|---|---|
| pH | 2.0-5.0 | | 4.2 |
| Preservative Content | Sodium Benzoate | 0.050% w/v-0.150% w/v | 0.097% |
| Microbial Limits | Total Aerobic Microbial Count | NMT 100 cfu/mL | Conforms |
| | Total Combined Yeast & Mold | NMT 20 cfu/mL | Conforms |
| | *Escherichia coli* | Absent | Conforms |
| | *Burkholderia cepacia* | Absent | Conforms |

As described in the tables above, the oral compositions including 20 mEq/15 mL potassium chloride and 40 mEq/15 mL potassium chloride were not adversely affected by the tested in-use conditions.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the invention are intended to be covered by the foregoing description and the following claims.

What is claimed is:

1. An aqueous oral composition consisting of:
potassium chloride;
about 1% to about 5% (w/v) glycerin;
about 0.04% to about 0.16% (w/v) sucralose;
about 0.1% to about 1.0% (w/v) sodium citrate dihydrate;
about 0.05% to about 0.5% (w/v) citric acid;
about 0.02% to about 0.2% (w/v) sodium benzoate;
colorant;
flavoring; and
water;
wherein the composition includes up to about 40 mEq potassium per 15 ml of the composition; and
wherein the composition is a solution.

2. The aqueous oral composition of claim 1, wherein the composition has a pH of 2 to 4.2.

3. The aqueous oral composition of claim 1, wherein the composition has a pH of 2.0 to 4.3.

4. The aqueous oral composition of claim 1, wherein the citric acid content of the composition is about 0.05% to about 0.3% (w/v).

5. The aqueous oral composition of claim 1, wherein the citric acid content of the composition is about 0.15% to about 0.5% (w/v).

6. The aqueous oral composition of claim 1, wherein the colorant is FD&C Yellow No. 6.

* * * * *